(12) United States Patent
Prevoo

(10) Patent No.: US 12,220,169 B2
(45) Date of Patent: Feb. 11, 2025

(54) METHOD FOR PERFORMING AN ASTIGMATISM POWER TEST USING A COMPUTING DEVICE HAVING A SCREEN FOR DISPLAYING IMAGES RELATING TO SAID ASTIGMATISM POWER TEST, AS WELL AS A CORRESPONDING COMPUTING DEVICE

(71) Applicant: EASEE HEALTH B.V., Amsterdam (NL)

(72) Inventor: Yves Franco Diano Maria Prevoo, Amsterdam (NL)

(73) Assignee: EASEE HEALTH B.V., Amsterdam (NL)

( * ) Notice: Subject to any disclaimer, the term of this patent is extended or adjusted under 35 U.S.C. 154(b) by 1000 days.

(21) Appl. No.: 17/260,789

(22) PCT Filed: Jul. 16, 2019

(86) PCT No.: PCT/NL2019/050448
§ 371 (c)(1),
(2) Date: Jan. 15, 2021

(87) PCT Pub. No.: WO2020/017959
PCT Pub. Date: Jan. 23, 2020

(65) Prior Publication Data
US 2021/0275012 A1    Sep. 9, 2021

(30) Foreign Application Priority Data

Jul. 16, 2018 (NL) ...................................... 2021310

(51) Int. Cl.
*A61B 3/036* (2006.01)
*A61B 3/00* (2006.01)
(Continued)

(52) U.S. Cl.
CPC ............ *A61B 3/036* (2013.01); *A61B 3/0041* (2013.01); *A61B 3/032* (2013.01); *A61B 3/111* (2013.01);
(Continued)

(58) Field of Classification Search
CPC ........ A61B 3/036; A61B 3/103; A61B 3/1035
See application file for complete search history.

(56) References Cited

U.S. PATENT DOCUMENTS

2014/0268060 A1   9/2014 Lee
2016/0157711 A1*  6/2016 Maddalena .......... A61B 3/0025
                                                      351/241

(Continued)

FOREIGN PATENT DOCUMENTS

KR   2011-0009106 U    9/2011
WO   WO 2016/068813 A1  5/2016

OTHER PUBLICATIONS

International Search Report in International Patent Application No. PCT/NL2019/050448, mailed Sep. 20, 2019 (2 pages).
(Continued)

*Primary Examiner* — Ephrem Z Mebrahtu
(74) *Attorney, Agent, or Firm* — NIXON PEABODY LLP

(57) ABSTRACT

A method for performing an astigmatism power test using a computing having a screen for displaying images relating to the astigmatism power test. The method includes determining an angle of astigmatism, calibrating visual acuity of the user, determining amplitudes required for the astigmatism correction, and determining the needed refraction, as well as a corresponding computer system.

6 Claims, 3 Drawing Sheets

(51) Int. Cl.
*A61B 3/032* (2006.01)
*A61B 3/11* (2006.01)
*A61B 5/00* (2006.01)
*G06F 3/01* (2006.01)

(52) U.S. Cl.
CPC .............. *A61B 3/112* (2013.01); *A61B 5/748* (2013.01); *A61B 5/749* (2013.01); *G06F 3/015* (2013.01); *G06F 3/017* (2013.01); *A61B 2560/0223* (2013.01)

(56) References Cited

U.S. PATENT DOCUMENTS

2016/0270656 A1* 9/2016 Samec .................... A61B 3/022
2017/0027436 A1* 2/2017 Lee .......................... A61B 3/18

OTHER PUBLICATIONS

International Preliminary Report on Patentability in International Patent Application No. PCT/NL2019/050448, mailed Nov. 26, 2020 (17 pages).

* cited by examiner

METHOD FOR PERFORMING AN ASTIGMATISM POWER TEST USING A COMPUTING DEVICE HAVING A SCREEN FOR DISPLAYING IMAGES RELATING TO SAID ASTIGMATISM POWER TEST, AS WELL AS A CORRESPONDING COMPUTING DEVICE

CROSS REFERENCE TO RELATED APPLICATIONS

This application is a U.S. National Stage Application of International Patent Application No. PCT/NL2019/050448 filed on Jul. 16, 2019, which claims priority to NL Patent Application No. 2021310 filed on Jul. 16, 2018, each of which is incorporated herein by reference in its entirety.

BACKGROUND

The present disclosure is directed to a method of performing an astigmatism power test. More specifically, the present disclosure is directed to an astigmatism power test which can be performed by a user itself using a computing device.

A number of tests are currently utilized during eye examinations to determine the presence of astigmatism and to quantify its amount and axis. A Snellen chart or other eye charts may initially reveal reduced visual acuity. A standard Snellen chart is printed with eleven lines of block letters. The first line typically consists of one very large letter, which may be one of several letters, for example A, T, or E. Subsequent rows have increasing numbers of letters that decrease in size. A user taking the test covers one eye from a predetermined distance away, and reads aloud the letters of each row, beginning at the top. The smallest row that can be read indicates the visual acuity in that specific eye.

A keratometer may be used to measure the curvature of the steepest and flattest meridians in the cornea's front surface. A keratometer, also known as a ophthalmometer, is a diagnostic instrument for measuring the curvature of the anterior surface of the cornea, particularly for assessing the extent and axis of astigmatism. A keratometer uses the relationship between object size, image size, the distance between the reflective surface and the object, and the radius of the reflective surface. If three of these variables are known, or fixed, the fourth can be calculated.

There are three primary types of astigmatism: myopic astigmatism, hyperopic astigmatism, and mixed astigmatism. Myopic astigmatism indicates that one or both principal meridians of the eye are nearsighted. Hyperopic astigmatism indicates that one or both principal meridians are farsighted. Mixed astigmatism indicates that one principal meridian is nearsighted, and the other is farsighted.

Astigmatism may be corrected, for example, with eyeglasses, contact lenses, or refractive surgery. Various considerations involving eye health, refractive status, and lifestyle determine whether one option may be better than another. In those with keratoconus, certain contact lenses often enable patients to achieve better visual acuity than eyeglasses.

One of the disadvantages of the above described tests is that they need to be performed by an optician or ophthalmologist. These tests are comprehensive and complex such that users are not able to perform these themselves.

SUMMARY OF THE DISCLOSURE

It is an object of the present disclosure to achieve a method for performing an astigmatism power test for determining a needed refraction, that can be performed by the user itself.

It is another object of the present disclosure to achieve a system for performing the astigmatism power test.

To better address one or more of the concerns of the prior art, in a first aspect of the disclosure, there is provided a method for performing an astigmatism power test using a computing device having a screen for displaying images relating to said astigmatism power test.

The method comprising the steps of:
  determining, by said device, using feedback input received from a user, a calibrated rotation of an elongated image displayed on said screen such that in said calibrated position said user perceives said displayed elongated image substantially the most clear;
  determining, by said device, an angle of astigmatism based on said calibrated rotation of said elongated image;
  calibrating, by said device, using feedback input received from said user, a resolution acuity of said user irrespective of said astigmatism by amending a thickness of at least one first elongated image at substantially +45° of said determined angle of astigmatism and/or amending a thickness of at least one second elongated image at substantially −45° of said determined angle of astigmatism such that in a calibrated position said user is just able to recognize said at least one first elongated image and/or said at least one second elongated image;
  thickening and/or blurring, by said device, using feedback input received from said user, at least one first elongated image in an image with respect to at least one second elongated image, wherein said at least one first elongated image is at substantially +0° of said determined angle of astigmatism and said at least one second elongated image is at substantially +90° of said determined angle of astigmatism, using said calibrated resolution acuity, such that in a calibrated position said user perceives said at least one first elongated image the same as said at least one second elongated image;
  determining, by said device, a needed refraction based on a difference in thickness and/or blurriness between said at least one first elongated image at substantially +0° and said at least one second elongated image at substantially +90°.

The above described tests are explained in more detail here below.

In a first step, using feedback from the user, a calibrated position of an elongated image displayed on the screen is determined such that in said calibrated position said user perceives said displayed elongated image substantially the most clear.

This step may be implemented in a variety of ways. First, one may use the principle of a fan and block chart. A fan and block chart is a chart in which a plurality of lines are displayed, wherein the direction of the lines are different, The lines are rotated with respect to each other to form a sort of fan. A user having astigmatism is then to indicate which of the lines is the clearest line. That is, which line in the fan and block chart is perceived the most clear. A user having astigmatism will not perceive all the lines as if they are equally clear. A user having astigmatism will perceive differences in the lines while in reality there are no notable differences between the lines, except for the fact that they are rotated with respect to each other.

The line that is chosen by the user indicates the calibrated rotation, more specifically it indicates an angle of astigmatism.

Another option is to display a single elongated image, for example an arrow, and the user is able to rotate the elongated image using any form of input tool. For example, a smartphone, a keyboard, a mouse, a webcam or anything alike. The user is then to rotate the arrow until it perceives as if the arrow is the most clear.

It is noted that, for a user having astigmatism, light rays fail to produce a focused image point, but rather produce a series of elongated images ranging from linear to elliptical, depending upon the position within the optical train. In a zone known as the circle of least confusion, positioned between the tangential line image and the sagittal line image, the major and minor axes of the ellipse are equal and the image approaches a circular geometry. The determined angle of astigmatism is then related to the circle of least confusion.

In a next step, using feedback input received from the user, a resolution acuity of the user irrespective of astigmatism is calibrated by amending a thickness of at least one first elongated image at substantially +45 degrees of said determined angle of astigmatism and/or amending a thickness of at least one second elongated image at substantially −45 degrees of said determined angle of astigmatism such that in a calibrated position said user is just, or no longer, able to recognize said at least one first elongated image and/or said at least one second elongated image.

The inventors have found that the resolution acuity, i.e. the visual acuity, of a user is to be taken into account during the test for determining the actual needed refraction to compensate for the astigmatism. The resolution acuity is, ideally, determined irrespective of the angle of astigmatism. To accomplish that particular concept, one or more lines are displayed, for the user, at 45 degrees of the angle of astigmatism and/or one or more lines are displayed, for the user, at −45 degrees of the angle of astigmatism. It is understood that these lines have the least impact of the deformation of the lens, i.e. the astigmatism aspects.

The user is then to provide input to the computing device with respect to the thickness of the lines that are displayed. More specifically, the user is to reduce the thickness of the lines until he/she is just, or no longer, able to see the lines. The actual thickness of the lines then forms a measure for the resolution acuity of that particular user. As mentioned above, the resolution acuity of the particular user may be taken into account when determining the needed refraction to compensate for the astigmatism.

In a next step, using feedback input received from the user, at least one first elongated image with respect to at least one second elongated image is amended in thickness and/or blurriness, wherein the at least one first elongated image is oriented such that it is substantially parallel to the angle of astigmatism, and the at least one second elongated image is oriented such that it is at substantially 90 degrees of said determined angle of astigmatism, using the calibrated resolution acuity, such that in a calibrated position said user perceives said at least one first elongated image the same as said at least one second elongated image.

It is noted that the at least one first elongated image and the at least one second elongated image may, initially, be displayed having a thickness as determined in the previous step. That is, a thickness in which the use was just, or no longer, able to recognize/see the lines on the screen. It is likely that a user will be able to see the first elongated image as the at least one first elongated image is oriented parallel to the angle of astigmatism. In the first step, the user has indicated that he/she has the best visual in that particular direction, which means that it may be able to recognize the at least one first elongated image as that particular image is now displayed parallel to the angle of astigmatism. It is also likely that the at least one second elongated image is not recognizable, i.e. the user is not able to see the second elongated image. It is noted that the first and second elongated image may have the same thickness, but that, due to the astigmatism, the user is not able to recognize the second elongated image but is able to recognize the first elongated image.

Then, the user provides input, i.e. feedback, based on which the thickness and/or blurriness of the first elongated image and/or the second elongated image is amended/adjusted. This process continues until the user perceives the first elongated image the same as the second elongated image.

Finally, the needed refraction is determined based on a difference in thickness and/or blurriness between the at least one first elongated image and the at least one second elongated image.

It is noted that, in the final step, the distance of the user to the screen as well as a calibrated spherical equivalent may be taken into account.

The distance of the user to the screen may be measured, which is explained in more detail with respect to the examples, or may be educationally guessed. For example, it was found that a user sits typically about 60 cm-80 cm away from his laptop screen. The distance may be taken into account when calibrating for the resolution acuity, i.e. the visual acuity of a user.

It is noted that the test as explained above may be performed twice, i.e. initially for a first eye of a user and subsequently for the other eye of the user. During the test, one of the two eyes may be blindfolded, such that only one eye is tested at the same time.

It is noted that the "images" of the "elongated image", the "at least one first elongated image at substantially +45° of said determined angle of astigmatism", the "at least one second elongated image at substantially −45° of said determined angle of astigmatism", the "at least one first elongated image at substantially +0° of said determined angle of astigmatism", and the "at least one first elongated image at substantially +90° of said determined angle of astigmatism", may at least initially be substantially the same. That is, before thickening and/or blurring said images, they may all be substantially the same. Alternatively they may however also be different from each other, or subsets of the group of in total at least five images may be the same while other images are different.

For example, the "elongated image" may initially be a substantially vertically oriented line or arrow, as described in the above, or may be a fan and black chart as described in the above, while the other images, i.e. the at least one first elongated image at substantially +45° of said determined angle of astigmatism, the at least one second elongated image at substantially −45° of said determined angle of astigmatism, the at least one first elongated image at substantially +0° of said determined angle of astigmatism, and the at least one first elongated image at substantially +90° of said determined angle of astigmatism may (initially) consist of substantially parallel lines having a pre-defined thickness, oriented at the specified angle with respect to the determined angle of astigmatism. The thickness of the lines may then subsequently be changed, e.g. thickened or thinned, and/or the lines may be blurred, as was described in the above.

The angle at which the images are displayed is however different, as is specified. The "elongated image" may initially be displayed in a substantially vertical orientation, and calibrated by a user to reach a calibrated position. Based on this calibrated position/rotation, the angle of astigmatism is determined. The "elongated image" may alternatively be referred to as "a first elongated image". The at least one first elongated image at substantially +45° of said determined angle of astigmatism is then displayed at an angle of substantially +45° with respect to said determined angle of astigmatism. The "at least one first elongated image at substantially +45° of said determined angle of astigmatism" may alternatively be referred to as "a second elongated image, oriented at substantially +45° of said determined angle of astigmatism". The at least one second elongated image at substantially −45° of said determined angle of astigmatism, which may be the same image as the at least one first elongated image at substantially +45° of said determined angle of astigmatism and/or the elongated image, or which may be a different image, is then displayed at an angle of substantially −45° with respect to said determined angle of astigmatism. The "at least one second elongated image at substantially −45° of said determined angle of astigmatism" may alternatively be referred to as "a third elongated image, oriented at substantially −45° of said determined angle of astigmatism". The at least one first elongated image at substantially +0° of said determined angle of astigmatism, which again may be a similar or same image as the above-mentioned images or which may be a different image, is then displayed at an angle of substantially +0° with respect to said determined angle of astigmatism. The "at least one first elongated image at substantially +0° of said determined angle of astigmatism" may alternatively be referred to as "a fourth elongated image, oriented at substantially +0° of said determined angle of astigmatism". And the at least one second elongated image at substantially +90° of said determined angle of astigmatism, which again may be a similar or same image as the above-mentioned images or which may be a different image, is then displayed at an angle of substantially +90° with respect to said determined angle of astigmatism. The "at least one second elongated image at substantially +90° of said determined angle of astigmatism" may alternatively be referred to as "a fifth elongated image, oriented at substantially +45° of said determined angle of astigmatism".

Preferably, the second, third, fourth, and fifth elongated images each (initially) comprise parallel lines, which are arranged at the specified angels with respect to the determined angle of astigmatism. Hence, preferably the second, third, fourth and fifth elongated images are the same (initially). However, said images may also be different elongated images.

So, while the physical representation of the images themselves may be different or the same, the angle at which the respective images (lines) are displayed changes in the way as specified.

In an example any of said feedback input is received via:
a touch screen of a User Equipment;
a camera unit comprised by said device, wherein said camera unit is arranged to detect gestures of said user;
voice recognition;
brainwave control.

It is noted that the computing device, in accordance with the present disclosure may be a desktop computer, a smart-phone, a tablet, a laptop or anything alike. The user may provide its input via a smartphone, a keyboard or something similar.

Preferably, the method is implemented in a webserver, wherein a browser displays the images to the user. The user may then either provide its input via a smartphone or may provide its input via a keyboard.

In another example, the device comprises a camera unit, and wherein said method further comprises the steps of:
capturing, by said camera unit of said device, at least one image of a human face of said user facing said screen;
detecting, by said device, in said at least one captured image, both pupils of said human face;
determining, by said device, a distance of said user to said screen based on:
a predetermined distance between pupils of a user;
a distance between said detected pupils in said at least one captured image, and
a focal length of said camera unit corresponding to said at least one captured image, wherein said focal length of said camera unit is determined by calculating said focal length based on said predetermined distance between pupils of a user and a predetermined initial distance of a user facing said screen;
wherein said step of determining said needed refraction is further based on said determined distance of said user to said screen.

It was one of the insights of the inventors that the pupillary distance of people, i.e. the predetermined distance between pupils of a user, is generally about constant. Therefore, that parameter may be used for determining the distance of the user to the screen.

The inventors furthermore noticed that the type of camera unit used for capturing the at least one image may influence the eye examination test, because the focal length varies per type of camera unit and/or per captured image. It was an insight of the inventors to control for this variable by determining the focal length of the camera corresponding to the at least one captured image prior to the step of determining the distance of the user to the screen.

Following the above, at least three parameters should be taken into account in order to accurately determine the actual distance of the user to the screen.

The first parameter is the above described generally constant distance between pupils of a user. A second parameter is the distance between the pupils in the at least one captured image. This distance is, for example, expressed in pixels. Finally, the focal length of the camera unit used for capturing the image is used for converting the distance between the pupils in the captured image to an actual measure for the physical distance of the user to the screen.

In accordance with the present disclosure, the input tool may be a mobile UE. The mobile UE may be any of a smart phone, tablet, smart watch or anything alike. Such a mobile UE may be used, by the user, as an input device for inputting answers to questionnaires displayed on the screen. It is noted that, during the eye examination test, the user is at a particular distance from the computing device such that the user is not able to physically reach the computing device. The mobile UE is thus used as an extended input device. As another option, the input tool may be a microphone. The microphone may be comprised by the computing device. Answers to specific questionnaires may then be provided using voice recognition algorithms running on the computing device.

In an alternative fashion, the focal length of the camera may be obtained via meta data of images that were taken by the camera, or using an API to retrieve the focal length directly from the camera.

In a further example, the device comprises a camera unit, and wherein said method further comprises the steps of:
capturing, by said camera unit of said device, at least one image of a human face of said user facing said screen;
detecting, by said device, a tilting angle of a head of said user to said screen,
and wherein at least one of said steps of the method takes into account said detected tilting angle of said head.

The inventors have found that, in order to improve the accuracy of the astigmatism test, the tilting angle of the head should be taken into account. The determined angle of astigmatism is typically defined based on a position of the head in which the two pupils are substantially horizontal. The angle of astigmatism is then corrected based on the tilting angle of the head.

In yet another example, the device comprises a camera unit, and wherein said method further comprises the steps of:
capturing, by said camera unit of said device, at least one image of a human face of said user facing said screen;
detecting, by said device, a light intensity or distribution of a surrounding of said user using said captured at least one image,
and wherein at least one of said steps of the method takes into account said detected light intensity or distribution.

The inventors have found that the light distribution, or light intensity, may have an impact on the astigmatism power test. For example, the resolution acuity, i.e. the visual acuity, may be deteriorated when there is insufficient, inadequate, or non-uniform lighting. The determined visual acuity may then be corrected for based on the determined light intensity or distribution.

In another example, the device comprises a camera unit, and wherein said method further comprises the steps of:
capturing, by said camera unit of said device, at least one image of a human face of said user facing said screen;
detecting, by said device, a pupil size of said user in said at least one image,
and wherein at least one of said steps of the method takes into account said detected pupil size.

The pupil size is a measure for the effort of a user in perceiving the elongated images. When a user is putting a lot of effort in his/her visual, he/she tends to squeeze his/her eyes together. The obtained visual acuity may then be corrected based on the expression, i.e. the pupil size, of the user performing the test.

In a second aspect of the present disclosure, there is a system for performing an astigmatism power test using a method as described in the above, said system comprising a computing device having a screen arranged for displaying images relating to said astigmatism power test.

The computing device comprising:
determine equipment arranged for determining, using feedback input received from a user, a calibrated rotation of an elongated image displayed on said screen such that in said calibrated position said user perceives said displayed elongated image substantially the most clear;
a processor arranged for determining an angle of astigmatism based on said calibrated position of said elongated image;
calibrate equipment arranged for calibrating, using feedback input received from said user, a resolution acuity of said user irrespective of said astigmatism by amending a thickness of at least one first elongated image at substantially +45° of said determined angle of astigmatism and/or amending a thickness of at least one second elongated image at substantially −45° of said determined angle of astigmatism such that in a calibrated position said user is just, or no longer, able to recognize said at least one first elongated image and/or said at least one second elongated image;
adjust equipment arranged for thickening and/or blurring using feedback input received from said user, at least one first elongated image in an image with respect to at least one second elongated image, wherein said at least one first elongated image is at substantially +0° of said determined angle of astigmatism and said at least one second elongated image is at substantially +90° of said determined angle of astigmatism, using said calibrated resolution acuity, such that in a calibrated position said user perceives said at least one first elongated image the same as said at least one second elongated image;
refraction equipment arranged for determining a needed refraction based on a difference in thickness and/or blurriness between said at least one first elongated image at substantially +0° and said at least one second elongated image at substantially +90°.

In accordance with the present disclosure, different aspects applicable to the above mentioned examples of the methods, including the advantages thereof, correspond to the aspects which are applicable to the system according to the present disclosure.

In an example, any of said feedback is received via:
a touch screen of a User Equipment;
a camera unit comprised by said device, wherein said camera unit is arranged to detect gestures of said user;
voice recognition;
brainwave control.

In a further example, the device comprises a camera unit, and wherein said camera unit is arranged for capturing at least one image of a human face of said user facing said screen,
and wherein said device further comprises:
detect equipment arranged for detecting, in said at least one captured image, both pupils of said human face;
process equipment arranged for determining a distance of said user to said screen based one:
a predetermined distance between pupils of a user;
a distance between said detected pupils in said at least one captured image, and
a focal length of said camera unit corresponding to said at least one captured image, wherein said focal length of said camera unit is determined by calculating said focal length based on said predetermined distance between pupils of a user and a predetermined initial distance of a user facing said screen;
wherein said refraction equipment is further arranged for determining said needed refraction based on said determined distance of said user to said screen.

In yet another example, the device comprises a camera unit, and wherein said camera unit is arranged for capturing at least one image of a human face of said user facing said screen;
and wherein said device further comprises:
detect equipment arranged for detecting a tilting angle of a head of said user to said screen,
and wherein any of said equipment of said device is arranged to take into account said detected tilting angle of said head.

In an example, the device comprises a camera unit, and wherein said camera unit is arranged for capturing at least one image of a human face of said user facing said screen, and wherein said device further comprises:

detect equipment arranged for detecting a light intensity of a surrounding of said user using said captured at least one image, and wherein any of said equipment of said device is arranged to take into account said detected light intensity.

In a further example, the device comprises a camera unit, and wherein said camera unit is arranged for capturing at least one image of a human face of said user facing said screen;

and wherein said device comprises detect equipment is arranged for detecting a pupil size of said user in said at least one image, and wherein any of said equipment of said device is arranged to take into account said detected pupil size.

The expressions, i.e. the wording, of the different aspects comprised by the method and system according to the present disclosure should not be taken literally. The wording of the aspects is merely chosen to accurately express the rationale behind the actual functioning of the aspects.

The above-mentioned and other features and advantages of the disclosure will be best understood from the following description referring to the attached drawings. In the drawings, like reference numerals denote identical parts or parts performing an identical or comparable function or operation.

DETAILED DESCRIPTION OF THE DRAWINGS

Figure 1:
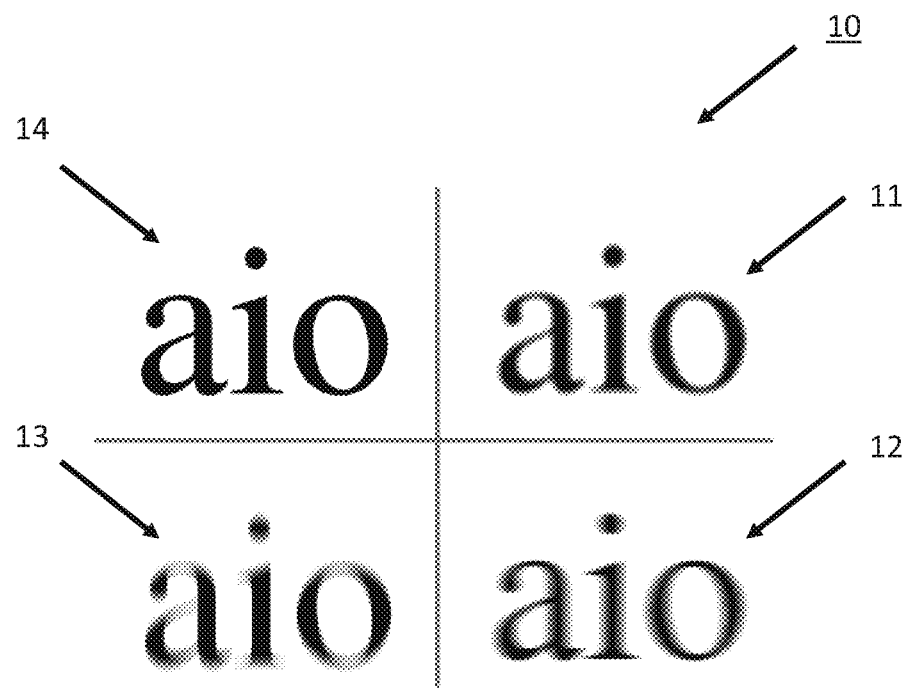
FIG. 1 discloses various known perceptions of astigmatism.

FIG. 1 discloses various known perceptions of astigmatism. Astigmatism is a common vision condition that causes blurred vision. It occurs, for instance, when the cornea, sometimes indicated as the clear front cover of the eye, is irregularly shaped or sometimes because of a curvature of the lens inside the eye. FIG. 1 shows a diagram 10 comprising four different conditions of a person's eye sight, being a condition wherein there is no astigmatic error 14, a combination of vertical and horizontal astigmatic error 11, a horizontal astigmatic error 13, and a vertical astigmatic error 12.

Figure 2:
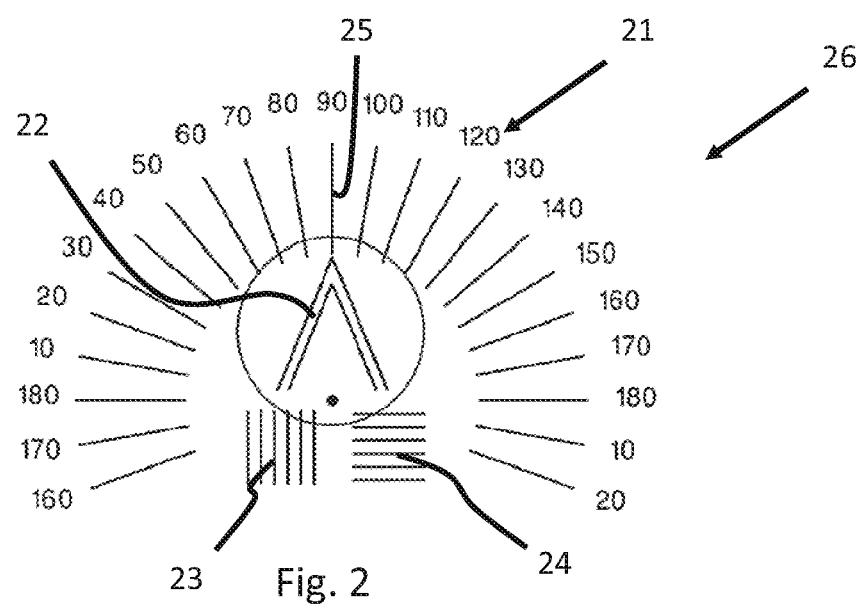
FIG. 2 discloses a diagram to assess the angle of astigmatic error of a user.

FIG. 2 shows a diagram which is used to assess the angle of astigmatic error. The diagram 26 comprises an arrow 22, angle indicating lines 25 positioned along a degree range 21, vertical reference lines 23, and horizontal reference lines 24.

The user is prompted to rotate the arrow 22 in respect to the angle indicating lines 25 to a degree at which the user has the best vision. The diagram is to be used by the user remotely via user equipment (not shown). The user can adjust the angle of the arrow 22 to the line which he/she is best able to see. To this end, the user equipment comprises, for instance, a touch screen having a slider indicated thereon. It is also possible that the user equipment comprises an input tool with sensors configured to receive and input gestures made by the user to adjust the position of the arrow 22.

It is possible that, in contrast to a rotating arrow 22, the angle indicating lines 25 are configured to rotate, together with the degree range 21, with respect to the arrow 22.

Figures 3A, 3B:
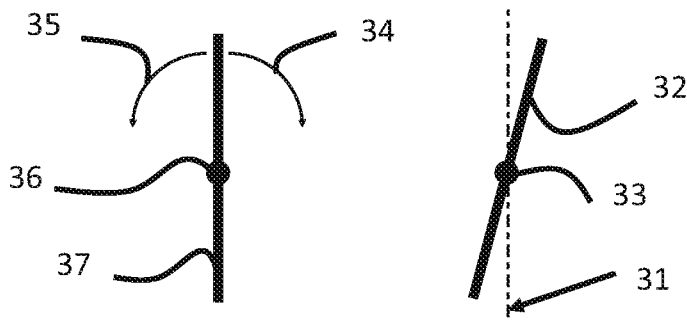
FIGS. 3a and 3b disclose an elongated image respectively oriented vertical, and altered for determining the angle of astigmatism.

FIGS. 3a and 3b disclose an elongated image respectively oriented vertical, and altered for determining the angle of astigmatism.

To this end, a user may rotate the elongated image 37 about the axis 36 either clockwise or counter clockwise like indicated with reference numeral 34 and 35. The user should rotate the elongated image 37 until it has the feeling that the line 37 is the most clear. This is shown in FIG. 3b. Here the user has rotated the line 32 about the axis 33 to a particular position. Wherein an offset of the line 32 with respect to the vertical axis 31 is considered the angle of astigmatism.

Figure 4:
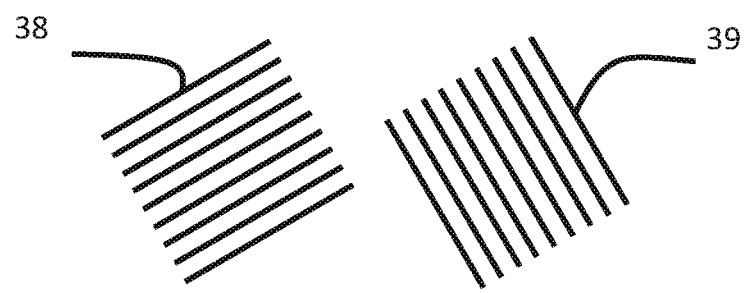
FIG. 4 discloses a presentation for calibrating of a user's visual acuity.

FIG. 4 discloses a presentation for calibrating of a user's visual acuity. Here, two sets of lines are shown as indicated with reference numeral 38 and 39. All lines have the same thickness and should be reduced in thickness, using input from a user, to a point in which the user is no longer able, or is just able, to see the lines. As such, in the end image, a user should have a completely grey, or white, background without any visible, at least to him/her, lines thereon.

Figure 5:
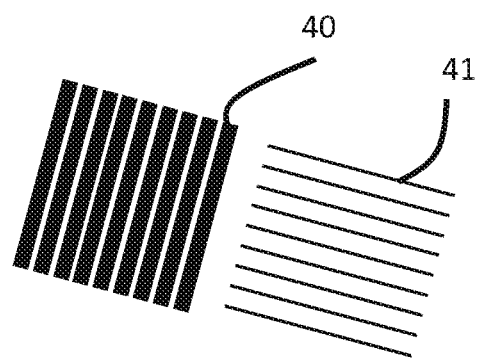
FIG. 5 discloses an example which is used for assessing the amplitude required for the needed refraction.

FIG. 5 discloses an example which is used for assessing the amplitude required for the needed refraction.

FIG. 5 shows at least one first elongated image 40 and at least one second elongated image 41. Both images 40, 41 comprise a plurality of lines placed next to each other, i.e. in parallel, just like the lines in FIG. 4. The lines as indicated with reference numeral 40 are in the same direction as the determined angle of astigmatism. This can be seen by relating the direction of the lines 40 with the line 32 of FIG. 3b. The lines as indicated with reference numeral 41 are 90 degrees rotated compared to the lines as indicated with reference numeral 40.

Initially, the thickness of both lines 40, 41 may be set equal, i.e. to the thickness which was calibrated with reference to FIG. 4. It is assumed that the lines as indicated with reference numeral 40 may then be seen, i.e. perceived, by a user while the lines as indicated with reference numeral 41 may not be seen, i.e. perceived, by a user.

It was established, during the calibration phase, that a user has his/her best visual in the angle of astigmatism. The lines as indicated with reference numeral 40 are oriented in the same angle, such that it is likely that the user will see this lines better compared to the lines as indicated with reference numeral 41.

The thickness of the lines 40 and 41 may then be amended until the user indicates that the quality of the lines 40, 41, i.e. the thickness or blurriness of the lines 40, 41 are roughly the same.

The user thus interprets as if the thickness/blurriness of the lines 40, 41 are the same while in fact, in reality, the thickness is not the same. The relative difference of the thickness is then of importance for the present disclosure.

The relative thickness difference between the obtained lines 40, 41 is then used in a last step, i.e. in the step of determining a needed refraction. The needed refraction is then calculated based on the difference in thickness between the lines as well as a distance of the user to the screen.

Figure 6:
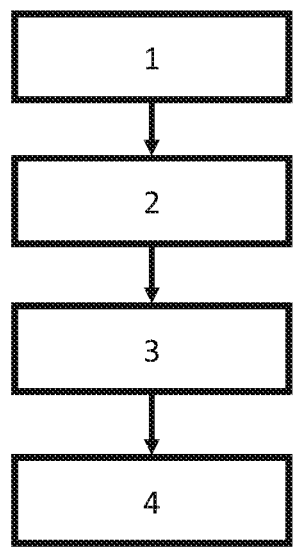
FIG. 6 discloses an example of a flow chart in accordance with the present disclosure.

FIG. 6 discloses a flow chart in accordance with the present disclosure. The flow chart comprises 4 particular steps which are referenced with using reference numerals 1, 2, 3, 4.

The first step 1 is directed to the determination, by the device, using feedback input received from a user, a calibrated rotation of an elongated image displayed on said screen such that in said calibrated position said user perceives said displayed elongated image substantially the most clear. Based on the calibrated position, the angle of astigmatism may be determined.

The angle of astigmatism is, often, not completely vertical of completely horizontal. Often, the angle has a particular offset which can be determined using step 1.

In step 2 a calibration process takes place. More specifically, the method comprises the step of calibrating, by said device, using feedback input received from said user, a resolution acuity of said user irrespective of said astigmatism by amending a thickness of at least one first elongated image at substantially +45° of said determined angle of astigmatism and/or amending a thickness of at least one second elongated image at substantially −45° of said determined angle of astigmatism such that in a calibrated position said user is just able to recognize said at least one first elongated image and/or said at least one second elongated image.

It was found by the inventors that the visual acuity of a person is to be taken into account during the astigmatism power test. The visual acuity is to be determined irrespective of the angle of astigmatism. This is accomplished by the +45 degrees and/or the −45 degrees concept.

In step 3, the amplitudes for the astigmatism correction are determined. More specifically, step 3 comprises thickening and/or blurring, by said device, using feedback input received from said user, at least one first elongated image with respect to at least one second elongated image, wherein said at least one first elongated image is at substantially +0° of said determined angle of astigmatism and said at least one second elongated image is at substantially +90° of said determined angle of astigmatism, using said calibrated resolution acuity, such that in a calibrated position said user perceives said at least one first elongated image the same as said at least one second elongated image.

Finally, in step 3, a needed refraction is determined, by the device, based on a difference in thickness and/or blurriness between said at least one first elongated image at substantially +0° and said at least one second elongated image at substantially +90°.

Figure 7:
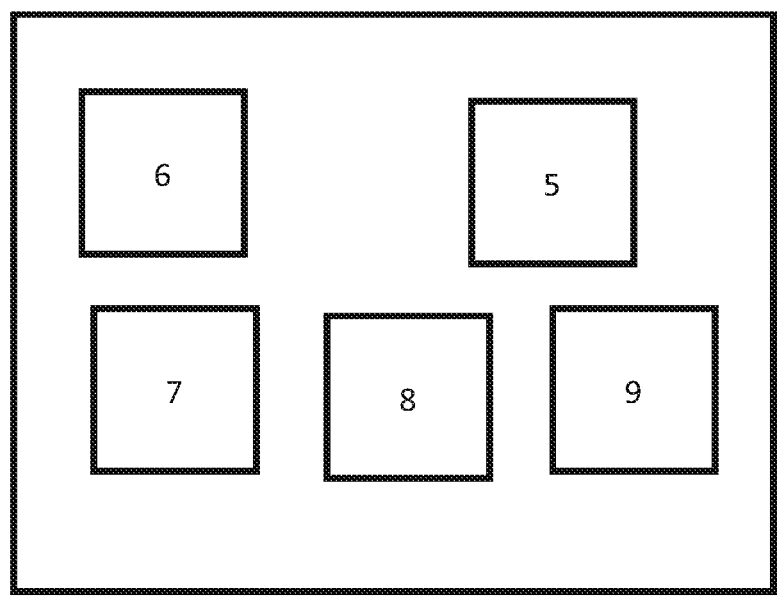
FIG. 7 discloses an example of a system in accordance with the present disclosure.

FIG. 7 discloses an example of a system in accordance with the present disclosure.

The system is arranged for performing an astigmatism power test using the method as described in the above. The system comprising a computing device having a screen arranged for displaying images relating to said astigmatism power test.

The computing device may be a single device, or may be split into multiple separate devices, such as a laptop, desktop, smartphone or anything alike.

The computing device comprises:
  determine equipment 6 arranged for determining, using feedback input received from a user, a calibrated rotation of an elongated image displayed on said screen such that in said calibrated position said user perceives said displayed elongated image substantially the most clear;
  a processor 5 arranged for determining an angle of astigmatism based on said calibrated position of said elongated image;
  calibrate equipment 7 arranged for calibrating, using feedback input received from said user, a resolution acuity of said user irrespective of said astigmatism by amending a thickness of at least one first elongated image at substantially +45° of said determined angle of astigmatism and/or amending a thickness of at least one second elongated image at substantially −45° of said determined angle of astigmatism such that in a calibrated position said user is just able to recognize said at least one first elongated image and/or said at least one second elongated image;
  adjust equipment 8 arranged for thickening and/or blurring using feedback input received from said user, at least one first elongated image with respect to at least one second elongated image, wherein said at least one first elongated image is at substantially +0° of said determined angle of astigmatism and said at least one second elongated image is at substantially +90° of said determined angle of astigmatism, using said calibrated resolution acuity, such that in a calibrated position said user perceives said at least one first elongated image the same as said at least one second elongated image;
  refraction equipment 9 arranged for determining a needed refraction based on a difference in thickness and/or blurriness between said at least one first elongated image at substantially +0° and said at least one second elongated image at substantially +90°.

Following the description above it is noted that another advantage of the present disclosure is that the astigmatism power test may be performed by a user without the aid of an optician or anyone alike. The astigmatism power test may be performed, for example, at home or in the office.

Even the ambient lighting which is used by the user may be taken into account during the test. It is noted that the ambient lighting is typically not uniform, white, or sufficient. A camera unit may detect the quality of the ambient lighting and may take the quality into account during the astigmatism power test, for example during the determination of the visual acuity.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope thereof.

What is claimed is:

1. A method for performing an astigmatism power test using a computing device having a screen for displaying images relating to said astigmatism power test, said method comprising:
  determining, by said computing device, using feedback input received from a user, a calibrated rotation of an elongated image displayed on said screen such that in a calibrated position said user perceives said displayed elongated image the most clear;

determining, by said computing device, an angle of astigmatism based on said calibrated rotation of said elongated image;

calibrating, by said computing device, using feedback input received from said user, a resolution acuity of said user irrespective of said astigmatism by amending a thickness of at least one first elongated image comprising one or more lines displayed at substantially +45° of said determined angle of astigmatism and/or amending a thickness of at least one second elongated image comprising one or more lines displayed at substantially −45° of said determined angle of astigmatism such that in a calibrated position said user is just able to recognize said at least one first elongated image and/or said at least one second elongated image;

thickening and/or blurring, by said computing device, using feedback input received from said user, at least one first elongated image with respect to at least one second elongated image, wherein said at least one first elongated image comprises a plurality of parallel lines arranged at substantially +0° of said determined angle of astigmatism and said at least one second elongated image comprises a plurality of parallel lines arranged at substantially +90° of said determined angle of astigmatism, using said calibrated resolution acuity, such that in a calibrated position said user perceives said at least one first elongated image the same as said at least one second elongated image;

determining, by said computing device, a needed refraction based on a difference in thickness and/or blurriness between said at least one first elongated image at substantially +0° and said at least one second elongated image at substantially +90°.

2. The method in accordance with claim 1, wherein any of said feedback input is received via:
   a touch screen of a User Equipment;
   a camera unit comprised by said computing device, wherein said camera unit is arranged to detect gestures of said user;
   voice recognition;
   brainwave control.

3. The method in accordance with claim 1, wherein said computing device comprises a camera unit, and wherein said method further comprises:
   capturing, by said camera unit of said computing device, at least one image of a human face of said user facing said screen;
   detecting, by said computing device, in said at least one captured image, both pupils of said human face;
   determining, by said computing device, a distance of said user to said screen based on:
   a predetermined distance between pupils of a user;
   a distance between said detected pupils in said at least one captured image, and
   a focal length of said camera unit corresponding to said at least one captured image, wherein said focal length of said camera unit is determined by calculating said focal length based on said predetermined distance between pupils of a user and a predetermined initial distance of a user facing said screen;
   wherein determining said needed refraction is further based on said determined distance of said user to said screen.

4. The method in accordance with claim 1, wherein said computing device comprises a camera unit, and wherein said method further comprises:
   capturing, by said camera unit of said computing device, at least one image of a human face of said user facing said screen;
   detecting, by said computing device, a tilting angle of a head of said user to said screen,
   and wherein at least one of the steps of the method takes into account said detected tilting angle of said head.

5. The method in accordance with claim 1, wherein said computing device comprises a camera unit, and wherein said method further comprises:
   capturing, by said camera unit of said computing device, at least one image of a human face of said user facing said screen;
   detecting, by said computing device, a light intensity of a surrounding of said user using said captured at least one image,
   and wherein at least one of the steps of the method takes into account said detected light intensity.

6. The method in accordance with claim 1, wherein said computing device comprises a camera unit, and wherein said method further comprises:
   capturing, by said camera unit of said computing device, at least one image of a human face of said user facing said screen;
   detecting, by said computing device, a pupil size of said user in said at least one image,
   and wherein at least one of steps of the method takes into account said detected pupil size.

* * * * *